US 11,291,947 B2

United States Patent
Shimizu et al.

(10) Patent No.: US 11,291,947 B2
(45) Date of Patent: Apr. 5, 2022

(54) COMPOSITION FOR REMOVING SULFUR-CONTAINING COMPOUND

(71) Applicant: KURARAY CO., LTD., Kurashiki (JP)

(72) Inventors: Masaki Shimizu, Kamisu (JP); Yuusuke Saitou, Kamisu (JP); Takuo Tsuruta, Kamisu (JP); Takahiro Suzuki, Kurashiki (JP); Junichi Fuji, Chiyoda-ku (JP)

(73) Assignee: KURARAY CO., LTD., Kurashiki (JP)

( * ) Notice: Subject to any disclaimer, the term of this patent is extended or adjusted under 35 U.S.C. 154(b) by 101 days.

(21) Appl. No.: 16/312,437

(22) PCT Filed: Jun. 21, 2017

(86) PCT No.: PCT/JP2017/022835
§ 371 (c)(1),
(2) Date: Dec. 21, 2018

(87) PCT Pub. No.: WO2018/003623
PCT Pub. Date: Jan. 4, 2018

(65) Prior Publication Data
US 2019/0329175 A1    Oct. 31, 2019

(30) Foreign Application Priority Data
Jun. 28, 2016    (JP) .............................. JP2016-127820

(51) Int. Cl.
*B01D 53/14*    (2006.01)
*C10G 29/24*    (2006.01)
*C10L 3/10*    (2006.01)

(52) U.S. Cl.
CPC ......... *B01D 53/1462* (2013.01); *C10G 29/24* (2013.01); *C10L 3/103* (2013.01); *B01D 2252/205* (2013.01); *B01D 2257/304* (2013.01)

(58) Field of Classification Search
CPC .......... B01D 53/1462; B01D 2252/205; B01D 2257/304; B01D 2257/306;
(Continued)

(56) References Cited

U.S. PATENT DOCUMENTS 2,402,615 A * 6/1946 Farlow .................. C07C 319/02
568/66
2,571,739 A * 10/1951 Marsh ................... C23F 11/122
422/9
(Continued)

FOREIGN PATENT DOCUMENTS

CN    101507932 A    8/2009
CN    103619466 A    3/2014
(Continued)

OTHER PUBLICATIONS

PubChem (2004) (Year: 2004).*
(Continued)

*Primary Examiner* — Pamela H Weiss
(74) *Attorney, Agent, or Firm* — Oblon, McClelland, Maier & Neustadt, L.L.P.

(57) ABSTRACT

Provided is a composition for removing a sulfur-containing compound present in liquid or vapor, the sulfur-containing compound being hydrogen sulfide, an —SH group-containing compound or a mixture thereof, the composition containing an α,β-unsaturated aldehyde represented by the following general formula (1) as an active ingredient;

(Continued)

wherein $R^1$ and $R^2$ each independently represent an alkyl group having 1 to 10 carbon atoms, an alkenyl group having 2 to 10 carbon atoms or an aryl group having 6 to 12 carbon atoms, or are connected to each other to represent an alkylene group having 2 to 6 carbon atoms; and $R^3$ represents a hydrogen atom or an alkyl group having 1 to 5 carbon atoms, or is connected to $R^1$ to represent an alkylene group having 2 to 6 carbon atoms.

11 Claims, 3 Drawing Sheets

(58) Field of Classification Search
CPC .................. B01D 2251/00; B01D 2251/21; B01D 53/48; B01D 53/52; C10G 29/24; C10L 3/103; C10L 3/10; C07C 45/85; C07C 47/22; B01J 20/22
See application file for complete search history.

(56) References Cited

U.S. PATENT DOCUMENTS

| | | | |
|---|---|---|---|
| 3,459,852 A | 8/1969 | Roehm | |
| 4,400,368 A * | 8/1983 | Diaz | B01D 53/1418 423/226 |
| 4,532,117 A | 7/1985 | Delaney | |
| 4,680,127 A | 7/1987 | Edmondson | |
| 4,734,259 A * | 3/1988 | Frenier | C09K 8/54 252/390 |
| 6,068,056 A * | 5/2000 | Frenier | C09K 8/52 166/307 |
| 6,399,547 B1 * | 6/2002 | Frenier | C09K 8/52 507/268 |
| 6,436,880 B1 * | 8/2002 | Frenier | C09K 8/52 507/131 |
| 2004/0055936 A1 | 3/2004 | Diehl et al. | |
| 2008/0227668 A1 * | 9/2008 | Welton | C09K 8/74 507/239 |
| 2008/0227669 A1 * | 9/2008 | Welton | C23F 11/122 507/239 |
| 2010/0099596 A1 * | 4/2010 | Trahan | C11D 7/36 510/188 |
| 2011/0015436 A1 | 1/2011 | Aoki et al. | |
| 2011/0174334 A1 | 7/2011 | Fan et al. | |
| 2012/0012506 A1 | 1/2012 | Compton et al. | |
| 2013/0004393 A1 | 1/2013 | Menendez et al. | |
| 2015/0266756 A1 * | 9/2015 | Trahan | C07C 45/52 210/747.5 |
| 2016/0261032 A1 * | 9/2016 | Chang | H01Q 1/273 |
| 2017/0081597 A1 | 3/2017 | Fuji et al. | |
| 2019/0329175 A1 | 10/2019 | Shimizu et al. | |
| 2019/0330541 A1 | 10/2019 | Shimizu et al. | |

FOREIGN PATENT DOCUMENTS

| | | |
|---|---|---|
| EP | 3 476 478 A1 | 5/2019 |
| EP | 3 546 052 A1 | 10/2019 |
| JP | 4-2352 A | 1/1992 |
| JP | 2003-292481 A | 10/2003 |
| JP | 2004-34028 A | 2/2004 |
| JP | 2004-340285 A | 12/2004 |
| JP | 2009-242384 A | 10/2009 |
| JP | 2012-520374 A | 9/2012 |
| JP | 2015-141535 A | 8/2015 |
| RU | 2 562 610 C2 | 8/2014 |
| WO | WO 2015/141535 A1 | 9/2015 |

OTHER PUBLICATIONS

Combined Russian Office Action and Search Report dated Apr. 10, 2020 in Russian Patent Application No. 2018145753 (with English translation), 16 pages.

Extended European Search Report dated Dec. 4, 2019 in European Patent Application No. 17819982.4, 8 pages.

International Search Report dated Aug. 29, 2017 in PCT/JP2017/022835 filed on Jun. 21, 2017.

Horaska, D.D. et al., "Acrolein Provides Benefits and Solutions to Offshore Oilfield-Production Problems", SPE Annual Technical Conference and Exhibition, SPE146080, 2011, pp. 47-54, URL: http://dx.doi.org/10.2118/146080-MS, (total 8 pages).

Combined Chinese Office Action and Search Report dated Mar. 3, 2021 in Patent Application No. 201780038428.7 (with English translation of Category of Cited Documents), 7 pages.

* cited by examiner

[Fig. 1]
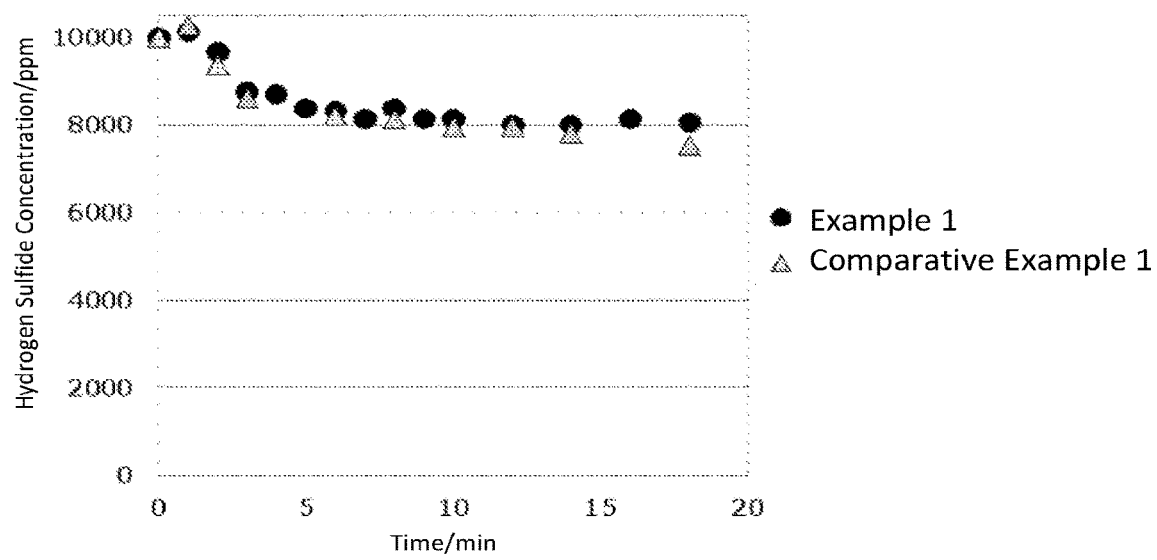

[Fig. 2]
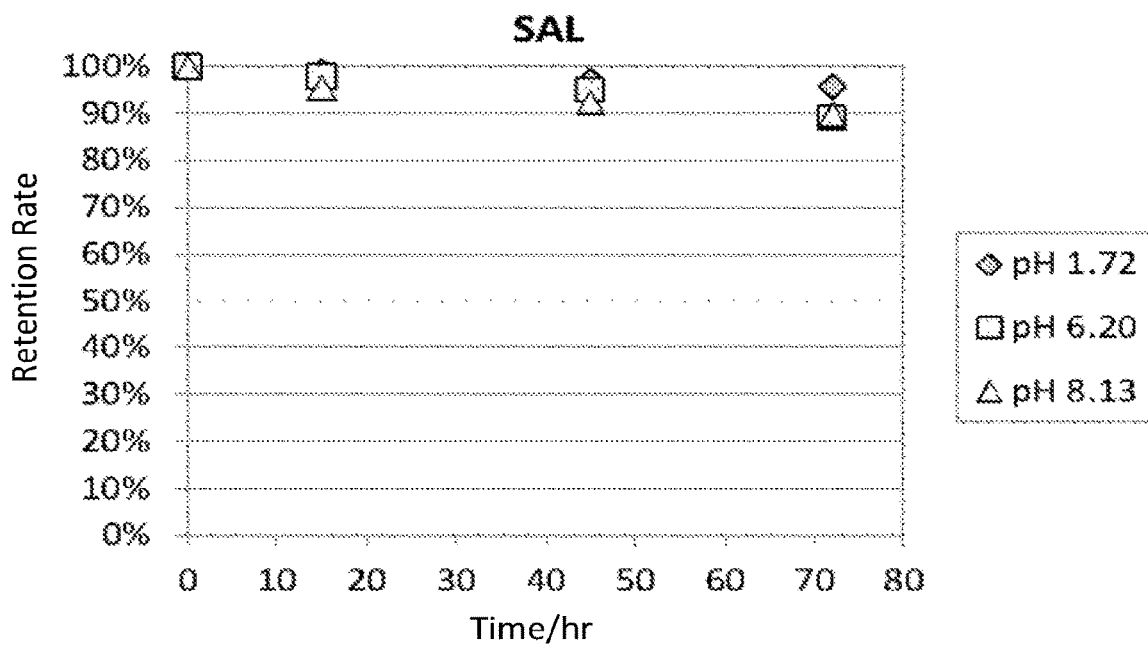

[Fig. 3]
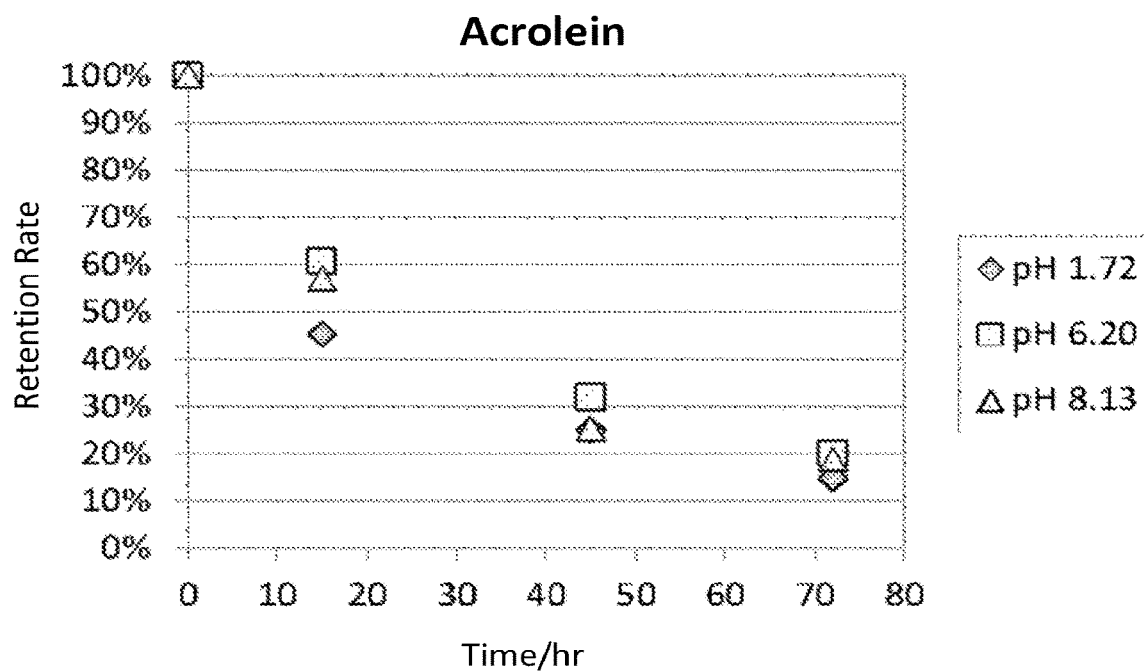

COMPOSITION FOR REMOVING SULFUR-CONTAINING COMPOUND

TECHNICAL FIELD

The present invention relates to a composition for removing a sulfur-containing compound, typically hydrogen sulfide, an —SH group-containing compound or a mixture thereof in liquid or vapor, or for reducing the concentration of the compound therein. Precisely, for example, the present invention relates to a composition for removing a sulfur-containing compound (typically hydrogen sulfide) contained in water or hydrocarbons such as fossil fuel and purified petroleum products (for example, natural gas, liquefied natural gas, sour gas, crude oil, naphtha, heavy aromatic naphtha, gasoline, kerosene, diesel oil, gas oil, heavy oil, FCC slurry, asphalt, oilfield condensate), and to a method for removing a sulfur-containing compound (typically hydrogen sulfide) using the composition.

BACKGROUND ART

Hydrocarbons in fossil fuel, purified petroleum products and the like such as natural gas, liquefied natural gas, sour gas, crude oil, naphtha, heavy aromatic naphtha, gasoline, kerosene, diesel oil, gas oil, heavy oil, FCC slurry, asphalt, and oilfield condensate often contain sulfur-containing compounds such as hydrogen sulfide and various —SH group-containing compounds (typically various mercaptans). The toxicity of hydrogen sulfide is well known, and in the industry that deals with fossil fuel and purified petroleum products, considerable costs and efforts are paid for reducing the content of hydrogen sulfide to a safe level. For example, for pipeline gas, a hydrogen sulfide content of not more than 4 ppm is required as an ordinary regulatory value. Hydrogen sulfide and various —SH group-containing compounds are volatile and therefore tend to emit in a vapor space, and in such a case, an offensive odor thereof is often problematic in the storage site and/or in the site around it and through the pipeline for use for transporting the hydrocarbon and the shipping system.

Hydrogen sulfide and various —SH group-containing compounds exist also in water such as sewage, the offensive odor derived from them often causes environmental pollution problems.

PTLs 1 and 2 disclose use of acrolein as a method for removing hydrogen sulfide. In SPE Annual Technical Conference and Exhibition SPE 146080 held in Denver, Colo. USA in Oct. 30 to Nov. 2, 2011, a report relating to hydrogen sulfide removal using acrolein as an active ingredient was announced. However, acrolein is a highly toxic compound and is therefore problematic in that the concentration thereof is strictly regulated from work safety and environment safety and that the compound requires careful handling. In addition, acrolein has other problems in that it extremely readily polymerizes and lacks thermal stability and that it also lacks pH stability and the amount thereof gradually reduces depending on the pH in the ambient environment.

CITATION LIST

Patent Literature

PTL 1: U.S. Pat. No. 4,680,127
PTL 2: U.S. Pat. No. 3,459,852

Non-Patent Literature

NPL 1: SPE Annual Technical Conference and Exhibition SPE146080, 2011; http://dx.doi.org/10.2118/146080-MS

SUMMARY OF INVENTION

Technical Problem

As described above, in using acrolein as an agent for removing hydrogen sulfide contained in liquid or vapor, there are problems from the viewpoints of safety, thermal stability and pH stability, and therefore, a safer and more stable compound is desired as a substitute therefor. Given the situation, an object of the present invention is to provide a composition containing an active ingredient with high thermal stability and pH stability and being capable of safely and efficiently removing a sulfur-containing compound, especially hydrogen sulfide, an —SH group-containing compound or a mixture thereof, which is contained in liquid or vapor.

Solution to Problem

According to the present invention, the above-mentioned object can be attained by the following [1] to [11].

[1] A composition for removing a sulfur-containing compound present in liquid or vapor, the sulfur-containing compound being hydrogen sulfide, an —SH group-containing compound or a mixture thereof, the composition containing an α,β-unsaturated aldehyde represented by the following general formula (1) (hereinafter referred to as "aldehyde (1)") as an active ingredient:

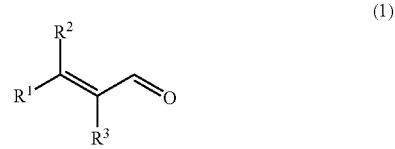

(1)

wherein $R^1$ and $R^2$ each independently represent an alkyl group having 1 to 10 carbon atoms, an alkenyl group having 2 to 10 carbon atoms or an aryl group having 6 to 12 carbon atoms, or are connected to each other to represent an alkylene group having 2 to 6 carbon atoms; and $R^3$ represents a hydrogen atom or an alkyl group having 1 to 5 carbon atoms, or is connected to $R^1$ to represent an alkylene group having 2 to 6 carbon atoms.

[2] The composition according to [1], wherein $R^1$ and $R^2$ each independently represent an alkyl group having 1 to 5 carbon atoms.

[3] The composition according to [1] or [2], wherein $R^3$ is a hydrogen atom.

[4] The composition according to any of [1] to [3], wherein the liquid or vapor is a hydrocarbon.

[5] The composition according to [4], wherein the hydrocarbon is at least one selected from the group consisting of natural gas, liquefied natural gas, sour gas, crude oil, naphtha, heavy aromatic naphtha, gasoline, kerosene, diesel oil, gas oil, heavy oil, FCC slurry, asphalt and oilfield condensate.

[6] A method for removing a sulfur-containing compound, wherein includes bringing the composition of any of [1] to [5] in contact with liquid or vapor, the sulfur-containing compound being hydrogen sulfide, an —SH group-containing compound or a mixture thereof.

[7] The method according to [6], wherein the liquid or vapor is a hydrocarbon.

[8] The method according to [7], wherein the hydrocarbon is at least one selected from the group consisting of natural gas, liquefied natural gas, sour gas, crude oil, naphtha, heavy aromatic naphtha, gasoline, kerosene, diesel oil, gas oil, heavy oil, FCC slurry, asphalt and oilfield condensate.

[9] The method according to any of [6] to [8], wherein the aldehyde (1) contained in the composition of any of [1] to [5] is added in an amount of 0.1 to 100 parts by mass relative to 1 part by mass of the sulfur-containing compound contained in the liquid or vapor.

[10] The method according to any of [6] to [9], including bringing the composition of any of [1] to [5] in contact with the sulfur-containing compound at a temperature in a range of −30° C. to 150° C.

[11] Use of the composition of any of [1] to [5], for removing a sulfur-containing compound being hydrogen sulfide, an —SH group-containing compound or a mixture thereof, which is present in liquid or vapor.

Advantageous Effects of Invention

The composition of the present invention contains the aldehyde (1) and is therefore excellent in the ability to remove a sulfur-containing compound, especially hydrogen sulfide, an —SH group-containing compound or a mixture thereof, which is present in liquid or vapor.

In particular, as compared with a conventional hydrogen sulfide remover that contains acrolein, the composition of the present invention has advantages in that the toxicity thereof is extremely low and the thermal stability and pH stability thereof are high. Though not always clear, one reason is because the aldehyde (1) is di-substituted at the β-position and therefore, as compared with acrolein not having a substituent at the β-position, the aldehyde (1) would hardly undergo addition reaction of bulky molecules such as a biomolecule or a propagating chain to the β-position thereof. On the other hand, it is considered that the attack from a sulfur-containing compound contained in liquid or vapor, which is in general a small molecule, is not hindered so much, whereby the ability to remove a sulfur-containing compound is kept.

BRIEF DESCRIPTION OF DRAWINGS

FIG. 1 is a graph showing the results of a hydrogen sulfide absorbing test with senecioaldehyde (SAL) and acrolein.
FIG. 2 is a graph showing the pH stability of SAL.
FIG. 3 is a graph showing the pH stability of acrolein.

DESCRIPTION OF EMBODIMENTS

Examples of the targeted liquid or vapor to which the composition of the present invention is applied include water and hydrocarbons. The hydrocarbons may be vapor, liquid, solid or a mixed state thereof, and typical examples thereof include, though not limited thereof, fossil fuel and purified petroleum products such as natural gas, liquefied natural gas, sour gas, crude oil, naphtha, heavy aromatic naphtha, gasoline, kerosene, diesel oil, gas oil, heavy oil, FCC slurry, asphalt, and oilfield condensate as well as any arbitrary combinations thereof.

In the present invention, the sulfur-containing compound to be contained in the targeted liquid or vapor and to be removed by the use of the composition of the present invention includes hydrogen sulfide, an —SH group-containing compound or a mixture thereof. Here, the —SH group-containing compound includes, though not limited thereto, sulfur-containing compounds as classified in mercaptans represented by a chemical formula "R—SH", for example, those where R is an alkyl group, such as methylmercaptan, ethylmercaptan, propylmercaptan, isopropylmercaptan, n-butylmercaptan, isobutylmercaptan, sec-butylmercaptan, tert-butylmercaptan, n-amylmercaptan; those where R is an aryl group, such as phenylmercaptan; those where R is an aralkyl group, such as benzylmercaptan; etc.

In the present invention, reducing the original amount of a sulfur-containing compound in a liquid or vapor by converting the sulfur-containing compound existing in the liquid or vapor into a different compound is included in the category "removing". After conversion into a different compound, the converted compound may be kept remaining in the system or may be separated out of the system.

The composition of the present invention is characterized by containing the aldehyde (1).

It is considered that a sulfur-containing compound may react mainly with the carbon-carbon double bond in the aldehyde (1) through addition reaction so that the sulfur-compound may be removed out of liquid or vapor.

In the case where the sulfur-containing compound is a mercaptans represented by "R—SH", the compound may change to $CR^1R^2(SR)$—$CH_2R^3$—CHO through addition reaction to the carbon-carbon double bond of the aldehyde (1), and the —SH group may be thereby removed.

On the other hand, in the case where the sulfur-containing compound is hydrogen sulfide, hydrogen sulfide may change to $CR^1R^2(SH)$—$CH_2R^3$—CHO through addition reaction to the carbon-carbon double bond of the aldehyde (1) and thereafter may react with another molecule of the aldehyde (1) to remove the —SH group.

In the aldehyde (1), the alkyl group having 1 to 10 carbon atoms that $R^1$ and $R^2$ each independently represent may be linear, branched or cyclic, and examples thereof include a methyl group, an ethyl group, a n-propyl group, an isopropyl group, a n-butyl group, an isobutyl group, a t-butyl group, a n-pentyl group, a n-hexyl group, a n-octyl group, a n-decyl group, a n-dodecyl group, and a cyclopentyl group. From the viewpoint of promoting the reaction with a sulfur-containing compound, above all, a methyl group, an ethyl group or a n-propyl group is preferred, a methyl group or an ethyl group is more preferred, and a methyl group is even more preferred.

The alkenyl group having 2 to 10 carbon atoms that $R^1$ and $R^2$ each independently represent may be linear, branched or cyclic, and examples thereof include a vinyl group, an allyl group, a 1-penten-1-yl group, a 4-methyl-3-penten-1-yl group, a 4-penten-1-yl group, a 1-hexen-1-yl group, a 1-octen-1-yl group, and a 1-decen-1-yl group. Above all, an alkenyl group having 1 to 8 carbon atoms is preferred, and an alkenyl group having 1 to 6 carbon atoms is more preferred.

Examples of the aryl group having 6 to 12 carbon atoms that $R^1$ and $R^2$ each independently represent include a phenyl group, a tolyl group, an ethylphenyl group, a xylyl group, a trimethylphenyl group, a naphthyl group, and a biphenylyl group. Above all, an aryl group having 6 to 10 carbon atoms is preferred.

In the case where $R^1$ and $R^2$ are connected to each other to represent an alkylene group having 2 to 6 carbon atoms, examples of the alkylene group include an ethylene group, a n-propylene group, a n-butylene group, a n-pentylene group, a n-hexylene group, a 2-methylethylene group, a 1,2-dimethylethylene group, a 2-methyl-n-propylene group, a 2,2-dimethyl-n-propylene group, and a 3-methyl-n-pentylene group.

From the viewpoint of promoting the reaction with a sulfur-containing compound, preferably $R^1$ and $R^2$ each independently represent an alkyl group having 1 to 5 carbon atoms, more preferably at least one of $R^1$ and $R^2$ is a methyl group, and even more preferably both $R^1$ and $R^2$ are methyl groups.

In the aldehyde (1) where $R^3$ represents an alkyl group having 1 to 5 carbon atoms, examples of the alkyl group include a methyl group, an ethyl group, a n-propyl group, an isopropyl group, a n-butyl group, an isobutyl group, a t-butyl group, a n-pentyl group and a cyclopentyl group.

In the case where $R^1$ and $R^3$ are connected to each other to represent an alkylene group having 2 to 6 carbon atoms, examples of the alkylene group include an ethylene group, a n-propylene group, a n-butylene group, a n-pentylene group, a n-hexylene group, a 2-methylethylene group, a 1,2-dimethylethylene group, a 2-methyl-n-propylene group, a 2,2-dimethyl-n-propylene group, and a 3-methyl-n-pentylene group.

From the viewpoint of promoting the reaction with a sulfur-containing compound, $R^3$ is preferably a hydrogen atom.

Examples of the aldehyde (1) include 3-methyl-2-butenal, 3-methyl-2-pentenal, 3-methyl-2-hexenal, 3-methyl-2-heptenal, 3-methyl-2-octenal, 3-methyl-2-nonenal, 3-methyl-2-decenal, 3-methyl-2-undecenal, 3-methyl-2-dodecenal, 3-methyl-2-tridecenal, 3-ethyl-2-pentenal, 3,4-dimethyl-2-pentenal, 3,4,4-trimethyl-2-pentenal, 3-isopropyl-4-methyl-2-pentenal, 3-ethyl-2-hexenal, 3-propyl-2-hexenal, 3,5-dimethyl-2-hexenal, 3-(t-butyl)-4,4-dimethyl-2-pentenal, 3-butyl-2-heptenal, 2,3-dimethyl-2-butenal, 2-ethyl-3-methyl-2-butenal, 2-isopropyl-3-methyl-2-butenal, 2,3-dimethyl-2-pentenal, 2,3,4-trimethyl-2-hexenal, 2-isobutyl-3-methyl-2-butenal, 3-methyl-2-pentyl-2-pentenal, 2,3-diethyl-2-heptenal, 2-(1,1-dimethylpropyl)-3-methyl-2-butenal, 3,5,5-trimethyl-2-hexenal, 2,3,4-trimethyl-2-pentenal, 2-cyclopropylidene-propanal, 2-cyclopentylidene-propanal, 2-cyclopentylidene-hexanal, 2-(3-methylcyclopentylidene)propanal, 2-cyclohexylidene-propanal, 2-(2-methylcyclohexylidene)propanal, 2-cyclohexylidene-butanal, 2-cyclohexylidene-hexanal, 1-cyclopropyl-2-formylcyclobutene, 1-formyl-2-methylcyclopentene, 1-formyl-5-isopropyl-2-methylcyclopentene, 1-formyl-2,5,5-trimethylcyclopentene, 1-formyl-2-methylcyclohexene, 1-formyl-2,5,6,6-tetramethylcyclohexene, 1-formyl-2,4,6,6-tetramethylcyclohexene, 3-methyl-2,4-pentadienal, 3-methyl-2,4-hexadienal, 3-methyl-2,5-hexadienal, 3,5-dimethyl-2,4-hexadienal, 3-methyl-2,4-heptadienal, 3-methyl-2,4-octadienal, 3-methyl-2,7-octadienal, 3,7-dimethyl-2,6-octadienal (citral), 3-methyl-2,4,6-octatrienal, 3,7-dimethyl-2,4,6-octatrienal, 3,8-dimethyl-2,7-nonadienal, 3-methyl-2,4-decadienal, 3-methyl-2,4-undecadienal, 3-methyl-2,4-dodecadienal, 3-methyl-2,4-tridecadienal, 3-phenylbutenal, 3-(o-tolyl)butenal, 3-(p-tolyl)butenal, and 3-naphthylbutenal. Above all, 3-methyl-2-butenal, 3-methyl-2-pentenal, 3-methyl-2-hexenal, 3-methyl-2-heptenal, 3-methyl-2-octenal, 3,7-dimethyl-2,6-octadienal (citral), 3-ethyl-2-pentenal, 3-ethyl-2-hexenal, and 3-propyl-2-hexanal are preferred; 3-methyl-2-butenal, 3-methyl-2-pentenal, and 3-ethyl-2-pentenal are more preferred; and 3-methyl-2-butenal (senecioaldehyde, hereinafter simply referred to as SAL) is even more preferred.

Regarding the compounds having a trans-form and a cis-form, any one alone may be used, or a mixture of the two may be used. In the case where a mixture is used, the mixture may have any arbitrary blending ratio.

As for the aldehyde (1), a commercially available product may be used, or it may be synthesized through an oxidative dehydrogenation reaction of a corresponding α,β-unsaturated alcohol (see, for example, JP 60-224652 A).

The composition of the present invention may contain any other sulfur-containing compound remover such as acrolein, formaldehyde, glyoxal, glutaraldehyde, 3-methylglutaraldehyde, 1,9-nonandial, or 2-methyl-1,8-octanedial, as long as the effects of the present invention are not impaired.

In the method of using the composition of the present invention to remove a sulfur-containing compound present in a hydrocarbon, a nitrogen-containing compound may be added as long as the effects of the present invention are further enhanced or are not impaired. Examples of the nitrogen-containing compound include α-aminoether compounds such as N,N'-oxybis(m ethylene)bis(N,N-dibutylamine), N,N'-(methylenebis(oxy)bis(methylene))bis(N,N-dibutylamine), 4,4'-oxybis(methylene)dimorpholine, bis(morpholinomethoxy)methane, 1,1'-oxybis(methylene)dipiperidine, bis(piperidinomethoxy)methane, N,N'-oxybis(methylene)bis(N,N-dipropylamine), N,N'-(methylenebis(oxy)bis(methylene))bis(N,N-dipropylamine), 1,1'-oxybis(methylene)dipyrrolidine, bis(pyrrolidinomethoxy)methane, N,N'-oxybis(methylene)bis(N,N-diethylamine), and N,N'-(methylenebis(oxy)bis(methylene))bis(N,N-diethylamine); alkoxy-hexahydrotriazine compounds such as 1,3,5-trimethoxypropyl-hexahydro-1,3,5-triazine, 1,3,5-trimethoxyethyl-hexahydro-1,3,5-triazine, 1,3,5-tri(3-ethoxypropyl)-hexahydro-1,3,5-triazine, 1,3,5-tri(3-isopropoxypropyl)-hexahydro-1,3,5-triazine, 1,3,5-tri(3-butoxypropyl)-hexahydro-1,3,5-triazine, and 1,3,5-tri(5-methoxypentyl)-hexahydro-1,3,5-triazine; alkyl-hexahydrotriazine compounds such as 1,3,5-trimethyl-hexahydro-1,3,5-triazine, 1,3,5-triethyl-hexahydro-1,3,5-triazine, 1,3,5-tripropyl-hexahydro-1,3,5-triazine, and 1,3,5-tributyl-hexahydro-1,3,5-triazine; hydroxyalkyl-hexahydrotriazine compounds such as 1,3,5-tri(hydroxymethyl)-hexahydro-1,3,5-triazine, 1,3,5-tri(2-hydroxyethyl)-hexahydro-1,3,5-triazine, and 1,3,5-tri(3-hydroxypropyl)-hexahydro-1,3,5-triazine; monoamine compounds such as monomethylamine, monoethylamine, dimethylamine, dipropylamine, trimethylamine, triethylamine, tripropylamine, monomethanolamine, dimethanolamine, trimethanolamine, diethanolamine, triethanolamine, monoisopropanolamine, dipropanolamine, diisopropanolamine, triisopropanolamine, N-methylethanolamine, dimethyl(ethanol)amine, methyldiethanolamine, dimethylaminoethanol, and ethoxyethoxyethanol-tert-butylamine; diamine compounds such as aminomethylcyclopentylamine, 1,2-cyclohexanediamine, 1,4-butanediamine, and 1,5-pentanediamine, 1,6-hexanediamine, bis(tert-butylaminoethoxy)ethane; imine compounds, imidazoline compounds; hydroxyaminoalkyl ether compounds; morpholine compounds; pyrrolidone compounds; piperidone compounds; alkylpiperidine compounds; 1H-hexahydroazepine; reaction products of alkylenepolyamine and formaldehyde such as reaction products of ethylenediamine and formaldehyde; aminocarboxylic acid polyvalent metal chelate compounds; quaternary ammonium salt compounds such as benzyl(cocoalkyl)(dimethyl) quaternary ammonium chloride, di(cocoalkyl)dimethylammonium chloride, di(tallow alkyl)dimethyl quaternary ammonium chloride, di(hydrogenated tallow alkyl)dimethyl quaternary ammonium chloride, dimethyl(2-ethylhexyl)(tallow alkyl)ammonium methyl sulfate, and (hydrogenated tallow alkyl)(2-ethylhexyl)dimethyl quaternary ammonium methyl sulfate; polyethyleneimine, polyallylamine, polyvinylamine; aminocarbinol compounds; aminal compounds; and bisoxazolidine compounds. One alone of these may be used alone, or two or more thereof may be used in combination.

In the case where the nitrogen-containing compound is added to a hydrocarbon, NOx forms in purification, and may have some negative influences on the environment. Taking this into consideration, more preferably, the nitrogen-containing compound is not added.

The composition of the present invention may further contain, in addition to the aldehyde (1), a component, such as a surfactant, a corrosion inhibitor, an oxygen scavenger, an iron control agent, a crosslinking agent, a breaker, a coagulant, a temperature stabilizer, a pH adjuster, a dehydration regulator, a swelling prevention agent, a scale inhibitor, a biocide, a friction reducer, a defoaming agent, an agent for preventing a lost circulation of mud water, a lubricating agent, a clay dispersant, a weighting agent, and a gelling agent, as long as the effects of the present invention are not impaired.

Before use, the composition of the present invention may be dissolved in an adequate solvent, for example, cyclohexane, toluene, xylene, heavy aromatic naphtha, or petroleum distillate; or a monoalcohol or diol having 1 to 10 carbon atoms such as methanol, ethanol, or ethylene glycol.

The content of the aldehyde (1), the active ingredient in the composition of the present invention may be adequately controlled depending on the use mode of the composition, and in general, the content is 1 to 99.9% by mass, but is, from the viewpoint of cost to performance, preferably 5 to 99.9% by mass, more preferably 5 to 95% by mass.

The method for producing the composition of the present invention is not specifically limited, and for example, the composition may be produced by adding and mixing the aldehyde (1) with the aforementioned arbitrary component such as a sulfur-containing compound remover or a solvent.

Preferably, the composition of the present invention is liquid, but depending on the use mode thereof for removing a sulfur-containing compound present in liquid or vapor, the composition may be in a solid form of powder or fluid held on an adequate carrier.

Examples of preferred embodiments of the present invention include a method of adding the composition of the present invention in an amount sufficient for removing a sulfur-containing compound (hydrogen sulfide, an —SH group-containing compound or a mixture thereof) to liquid or vapor, a method of making a gaseous hydrocarbon containing a sulfur-containing compound pass through a vessel filled with the composition of the present invention, and a method of spraying a mist of the composition of the present invention to a gas containing a sulfur-containing compound. In the method of removing a sulfur-containing compound present in liquid or vapor with the composition of the present invention, the amount of the aldehyde (1) contained in the composition of the present invention is preferably 0.1 to 100 parts by mass, more preferably 2 to 100 parts by mass relative to 1 part by mass of the sulfur-containing compound present in liquid or vapor. In the method of making a hydrocarbon pass through a vessel filled with the composition of the present invention for treatment, the amount of the composition of the present invention to be added is so controlled that the amount of the aldehyde (1) to be added falls within the above range relative to 1 part by mass of the sulfur-containing compound in the hydrocarbon to be made to pass through the vessel. A temperature on the occasion of performing the treatment in which the composition of the present invention is added to and brought in contact with a hydrocarbon is preferably in a range of −30° C. to 150° C., more preferably 0° C. to 130° C.

For removing a sulfur-containing compound in water using the composition of the present invention, for example, a method of injecting the composition of the present invention into a water reservoir in a sewage treatment plant or the like may be employed.

For removing a sulfur-containing compound in a hydrocarbon using the composition of the present invention and when the hydrocarbon is liquid, a known method of injecting the composition of the present invention into a reservoir tank, a pipeline for transportation or a distillation tower for purification may be employed. In the case where the hydrocarbon is vapor, the composition of the present invention is so arranged as to be brought in contact with the vapor, or the vapor may be made to pass through an absorption column filled with the composition of the present invention.

The composition of the present invention is also applicable to use for dissolving iron sulfide that causes a problem to lower the operation efficiency of mechanical systems such as heat exchangers, cooling columns, reactors and transportation pipelines in manufacturing sites for fossil fuel. Further, the composition of the present invention has bactericidal properties against sulfate reducers and others, and is therefore applicable to use for preventing biological corrosion in pipelines and others that is problematic in digging sites for fossil fuel.

In that manner, the composition of the present invention is generally applicable to various processes relating to digging or transportation of fossil fuel.

EXAMPLES

The present invention is hereunder specifically described by reference to Examples and the like, but it should be construed that the present invention is by no means limited by the following Examples. SAL, citral, and acrolein used in the Examples and Comparative Examples are those mentioned below.

SAL: One synthesized from prenol in conformity with the method described in JP 60-224652 A (purity: 98.1%)

Citral: Product available from Kuraray Co., Ltd. (purity: 98.0%, trans/cis=51/49 to 57/43 (molar ratio))

Acrolein: Product available from Tokyo Chemical Industry Co., Ltd., which contains hydroquinone as a stabilizer Example 1

A mixed gas having a composition of 1 vol % of hydrogen sulfide and 99 vol % of nitrogen was circulated through a 100-mL autoclave equipped with a thermometer, a stirrer and a feed pump, thereby to purge the vapor inside the autoclave with stirring at 800 rpm. The hydrogen sulfide concentration in the emission gas was continuously monitored with a detector RX-517 (available from Riken Kiki Co., Ltd.), and after the hydrogen sulfide concentration became stable, 40 mL of a composition liquid composed of 5 parts by mass of SAL and 95 parts by mass of tetralin (1,2,3,4-tetrahydronaphthalene, available from FUJIFILM Wako Pure Chemical Corporation) was fed into the autoclave via the feed pump. Based on the start time, 0 minute, the measured data of the hydrogen sulfide concentration change in the emission gas are shown in FIG. 1.

Comparative Example 1

The same test as in Example 1 was carried out except that acrolein was used in place of SAL. The results are shown in FIG. 1.

Example 2

20 g of distilled water was put into a 100-mL autoclave equipped with a thermometer and a stirrer, and pressurized up to 0.3 MPa with a mixed gas having a composition of 1 vol % of hydrogen sulfide and 99 vol % of nitrogen introduced thereinto. This was stirred until the hydrogen sulfide concentration in the vapor phase part became constant, and then the hydrogen sulfide concentration in the vapor phase part in the autoclave was measured with a Kitagawa gas detector (here, a hydrogen gas detector available from Komyo Rikagaku Kogyo K.K. was attached to the gas collector "AP-20"), and was 7,500 ppm by volume. Next, SAL was added thereto in an amount to be 5,000 ppm relative to the distilled water. The amount of SAL added was 1.19 mmol, and the amount of hydrogen sulfide existing in the apparatus was 0.10 mmol. Subsequently, the apparatus was heated up to 80° C. with stirring at 800 rpm to continue the reaction for 5 hours. After the reaction, the system was cooled down to room temperature, and the hydrogen sulfide concentration in the vapor phase part was measured and was 5,000 ppm by volume. The removal rate was 33%.

Comparative Example 2

The same test as in Example 2 was carried out except that acrolein was used in place of SAL. After the reaction, the hydrogen sulfide concentration in the vapor phase part was measured and was 5,000 ppm by volume. The removal rate was 33%.

Example 3

20 g of kerosene (available from FUJIFILM Wako Pure Chemical Corporation) was put into a 50-mL three-neck flask, and a mixed gas having a composition of 1 vol % of hydrogen sulfide and 99 vol % of nitrogen was made to circulate therein at a flow rate of 50 mL/min to thereby purge the vapor in the three-neck flask with stirring at 800 rpm. After 2 hours, the circulation of the mixed gas was stopped, then the three-neck flask was sealed up, and the hydrogen sulfide concentration in the vapor phase part in the three-neck flask was measured with a Kitagawa gas detector and was 8,200 ppm by volume. Next, 1.5 g of SAL was added thereto and reacted for 5 hours at room temperature with stirring the apparatus at 800 rpm. After the reaction, the hydrogen sulfide concentration in the vapor phase part in the three-neck flask was measured and was 5,300 ppm by volume. The removal rate was 35%.

Example 4

The same test as in Example 3 was carried out except that citral was used in place of SAL. After the reaction, the hydrogen sulfide concentration in the vapor phase part in the three-neck flask was measured and was 6,600 ppm by volume. The removal rate was 20%.

<Test Example 1> Thermal Stability Test 50 mL of each of SAL and acrolein was charged in 50-mL three-necked flask, and the contents were subjected to temperature rise to 50° C. in a nitrogen atmosphere. On the occasion when the content of each of SAL and acrolein immediately after the temperature rise was defined as 100%, a change of the content ratio was observed according to the calibration curve method by means of gas chromatography with an internal standard. The results are shown in Table 1.

[Gas Chromatography Analysis]

Analysis Instrument: GC-14A (Available from Shimadzu Corporation) Detector: FID (Hydrogen Flame Ionization Detector)

Column used: DB-1701 (length: 50 m, film thickness: 1 μm, inner diameter: 0.32 mm) (available from Agilent Technologies)

Analysis conditions: Injection temperature: 250° C., detection temperature: 250° C.

Temperature rise conditions: 70° C.→(temperature rise at 5° C./min)→250° C.

Internal standard substance: Diglyme (diethylene glycol dimethyl ether)

TABLE 1

Results of thermal stability test

| | 0 hour | 2 hours elapsed | 4 hours elapsed | 6 hours elapsed | 10 hours elapsed |
|---|---|---|---|---|---|
| SAL | 100.0% | 100.0% | 100.0% | 100.0% | 99.9% |
| Acrolein | 100.0% | 99.5% | 98.3% | 98.1% | 96.6% |

After elapsing 10 hours, SAL remained in a ratio of 99.9%, whereas nevertheless acrolein contained hydroquinone as a stabilizer, it was lost in a ratio of 3.4%. It is noted from these results that SAL is extremely high in the thermal stability as compared with acrolein.

<Test Example 2> pH Stability Test

Each of SAL and acrolein was dissolved in 0.5 mol/L of phosphoric acid buffer solutions having a pH different from each other, thereby preparing 0.1 wt % solutions. 50 mL of each of the solutions was charged in a sample vial in a nitrogen atmosphere and stored at 23±2° C. On the occasion when the content of each of SAL and acrolein at the time of preparation was defined as 100%, a change of the content ratio was observed according to the absolute calibration curve by means of high-performance liquid chromatography analysis. The results are shown in FIGS. 2 and 3.

It is noted from these results that SAL is extremely high in the pH stability as compared with acrolein.

[Preparation of Phosphoric Acid Buffer Solution]

pH 1.7: 4.9 g of 75% phosphoric acid and 7.8 g of sodium dihydrogen phosphate dihydrate were dissolved in 200 mL of distilled water.

pH 6.2: 7.8 g of sodium dihydrogen phosphate dihydrate and 7.1 g of disodium hydrogen phosphate were dissolved in 200 mL of distilled water.

pH 8.1: 0.3 g of sodium dihydrogen phosphate dihydrate and 13.9 g of disodium hydrogen phosphate were dissolved in 200 mL of distilled water.

[High-Performance Liquid Chromatography Analysis]

Analysis Instrument: Prominence System (Available from Shimadzu Corporation)

Column used: Cadenza CD-C18 (length: 150 m, inner diameter: 4.6 mm)

Developing solution: $H_2O/MeOH=45/55$ (volume ratio), $H_3PO_4=1$ mol/L

Flow rate: 1 mL/min

Reference Example

SAL, citral, and acrolein are each an existing compound, and the information regarding the safety is disclosed. For reference, the information regarding the safety is shown in Table 2. SAL and citral are extremely low in the toxicity and safe as compared with acrolein.

TABLE 2

Information regarding safety of SAL, citral, and acrolein

| | SAL | Citral | Acrolein |
|---|---|---|---|
| Fire Service Act | Category IV, Class II petroleum Hazardous grade III, water-insoluble | Category IV, Class III petroleum Hazardous grade III, water-insoluble | Category IV, Class I petroleum Hazardous grade II, water-insoluble |
| Poisonous and Deleterious Substances Control Law | Not applicable | Not applicable | Poisonous substance |
| United Nations Classification | Class 3 (inflammable liquid) | Not applicable | Class 6.1 (poisonous substance) |
| Acute toxicity | Rat LD50: 690 mg/kg | Rat LD50: 4,960 mg/kg | Rat LD50: 42 mg/kg |
| Permissible Exposure Limit | GHS Classification; Section 1 (upper respiratory tract) Irritative symptom in respiratory tract at 100 ppm or more | No information | 0.1 ppm Respiratory organs, nervous system, and liver are considered to be target organs Anesthetic action |

It is noted from the aforementioned Examples, Comparative Examples, Test Examples, and Reference Example that the aldehyde (1), such as SAL, has a sulfur-containing compound removing ability equivalent to acrolein and is higher in the thermal stability and the pH stability and safer than acrolein.

INDUSTRIAL APPLICABILITY

The composition of the present invention has high thermal stability and pH stability, and is useful in that it can safely and efficiently remove sulfur-containing compounds whose toxicity and offensive odor are problematic from liquid or vapor

The invention claimed is:

1. A method for removing a sulfur-comprising compound from a gas, the method comprising:
contacting a gaseous composition comprising the gas and the sulfur-comprising compound with a composition comprising at least one α,β-unsaturated aldehyde selected from the croup consisting of 3-methyl-2-butenal, 3-methyl-2-pentenal, 3-ethyl-2-pentenal, 2,3-dimethyl-2-butenal, 2-ethyl-3-methyl-2-butenal, 2-isopropyl-3-methyl-2-butenal, 2,3-dimethyl-2-pentenal, 2-isobutyl-3-methyl-2-butenal, 3-methyl-2-pentyl-2-pentenal, 2-(1,1)-dimethylpropyl)-3-methyl-2-butenal, and 3-methyl-2,4-pentadienal
wherein, in the contacting, the gaseous composition is not contacted with a nitrogen-comprising compound, and
wherein the sulfur-comprising compound is at least one selected from the group consisting of hydrogen sulfide, methylmercaptan, ethylmercaptan, propylmercaptan, isopropylmercaptan, n-butylmercaptan, isobutylmercaptan, sec-butylmercaptan, tert-butylmercaptan, n-amylmercaptan, phenylmercaptan, and benzylmercaptan.

2. The method of claim 1, wherein the gas is a hydrocarbon.

3. The method of claim 2, wherein the hydrocarbon is natural gas,
sour gas,
liquefied natural gas vapor,
crude oil vapor,
naphtha vapor,
heavy aromatic naphtha vapor,
gasoline vapor,
kerosene vapor,
diesel oil vapor,
gas oil vapor,
heavy oil vapor, or
a combination thereof.

4. The method of claim 1, wherein an amount of the α,β-unsaturated aldehyde comprised in the composition is 0.1 to 100 parts by mass relative to 1 part by mass of the sulfur-comprising compound comprised in the gaseous composition.

5. The method of claim 1, wherein the contacting occurs at a temperature in a range of from −30° C. to 150° C.

6. The method of claim 1, wherein the contacting is performed by passing the gaseous composition through a vessel or a column filled with the composition comprising the α,β-unsaturated aldehyde.

7. The method of claim 1, wherein the contacting is performed by spraying a mist of the composition comprising the α,β-unsaturated aldehyde into and/or onto the gaseous composition.

8. A method for removing a sulfur-comprising compound from a liquid, the method comprising:
contacting a liquid composition comprising the liquid and the sulfur-comprising compound with a composition comprising at least one α,β-unsaturated aldehyde selected from the group consisting of 3-methyl-2-butenal, 3-methyl-2-pentenal, 3-ethyl-2-pentenal, 2,3-dimethyl-2-butenal, 2-ethyl-3-methyl-2-butenal, 2-isopropyl-3-methyl-2-butenal, 2,3-dimethyl-2-pentenal, 2-isobutyl-3-methyl-2-butenal, 3-methyl-2-pentyl-2-pentenal, 2-(1,1-dimethylpropyl)-3-methyl-2-butenal, and 3-methyl-2,4-pentadienal
wherein the contacting is performed by injecting the composition comprising the alpha beta unsaturated aldehyde into: a) a reservoir tank containing the liquid composition, b) a pipeline in which the liquid composition is flowing, or c) a distillation tower in which the liquid composition is being purified, wherein the liquid is at least one selected from the group consisting of liquefied natural gas, crude oil, naphtha, heavy aromatic naphtha, gasoline, kerosene, diesel oil, gas oil, heavy oil, FCC slurry, asphalt, and oilfield condensate, wherein, in the contacting, the liquid composition is not contacted with a nitrogen-comprising compound, and wherein the sulfur-comprising compound is at least one selected from the group consisting of hydrogen sulfide, methylmercaptan, ethylmercaptan, propylmercaptan, isopropylmercaptan, n-butylmercaptan, isobutylmercaptan, sec-butylmercaptan, tert-butylmercaptan, n-amylmercaptan, phenylmercaptan, and benzylmercaptan.

9. The method of claim 8, wherein an amount of the $\alpha,\beta$-unsaturated aldehyde comprised in the composition is 0.1 to 100 parts by mass relative to 1 part by mass of the sulfur-comprising compound comprised in the liquid composition.

10. The method of claim 8, wherein the contacting occurs at a temperature in a range of from −30° C. to 150° C.

11. The method of claim 8, wherein the alpha-beta unsaturated aldehyde is at least one selected from the group consisting of 3-methyl-1-2-butenal, 3-methyl-2-pentenal, 3-ethyl-2-pentenal and 3-methyl-2-4-pentadienal.

\* \* \* \* \*